United States Patent [19]

Solofo et al.

[11] Patent Number: 5,210,350

[45] Date of Patent: May 11, 1993

[54] METHOD OF PREPARING AN ALKYLATED AROMATIC PRODUCT WITH AN ALKYLATION ZEOLITE AND A DEALKYLATION ZEOLITE

[75] Inventors: Jonis Solofo, Montpellier; Patrice Moreau, Saint-Gely-du-Fesc; Patrick Geneste; Annie Finiels, both of Montpellier, all of France

[73] Assignee: Michelin Recherche et Technique, Fribourg, Switzerland

[21] Appl. No.: 667,419

[22] Filed: Mar. 11, 1991

[30] Foreign Application Priority Data

Mar. 13, 1990 [FR] France ............... 90 03309

[51] Int. Cl.$^5$ .............................................. C07C 2/00
[52] U.S. Cl. ................................... 585/323; 585/315; 585/316; 585/467; 585/483
[58] Field of Search ............ 585/323, 483, 484, 486, 585/487, 488, 467, 814, 450, 451, 315, 316

[56] References Cited

U.S. PATENT DOCUMENTS

| | | | |
|---|---|---|---|
| 3,251,897 | 5/1966 | Wise | 260/671 |
| 3,716,596 | 2/1973 | Bowes | 260/671 C |
| 4,230,894 | 10/1980 | Young | 568/768 |
| 4,560,820 | 12/1985 | Field | 585/489 |
| 4,654,457 | 3/1987 | Sato | 585/486 |

FOREIGN PATENT DOCUMENTS 0160144 11/1985 European Pat. Off. .

*Primary Examiner*—Asok Pal
*Assistant Examiner*—P. Achutamurthy
*Attorney, Agent, or Firm*—Brumbaugh, Graves, Donohue & Raymond

[57] ABSTRACT

A method of preparing an alkylated aromatic product (12) by alkylation of an aromatic compound (1), the alkylation producing several alkylated aromatic products, this method being characterized by the following points:

(a) the aromatic compound (1) is reacted with an alkylating agent (2) in the presence of an alkylation zeolite (4);
(b) the alkylated aromatic product (12) is separated by crystallization from the products of the alkylation;
(c) the uncrystallized part (13) of the alkylated aromatic products is subjected to a dealkylation in the presence of a dealkylation zeolite (15);
(d) the regenerated aromatic compound ($1_b$) is recycled in order to react it again with the alkylating agent (2) in the presence of the alkylation zeolite (4). Alkylated aromatic compounds (12) obtained by this method, in particular 2–6 dicyclohexyl naphthalene.

18 Claims, 2 Drawing Sheets

METHOD OF PREPARING AN ALKYLATED AROMATIC PRODUCT WITH AN ALKYLATION ZEOLITE AND A DEALKYLATION ZEOLITE

BACKGROUND OF THE INVENTION

The present invention relates to a method of alkylating compounds, in particular aromatic compounds, with the use of zeolites as catalysts.

The production of aromatic compounds containing cyclic alkyl groups by the use of aluminum halides is known, for instance the synthesis of mono- or dicyclohexylnaphthalenes with $AlCl_3$, such reactions being described in particular in the following articles:

D. Bodroux, Annales de Chimie 1929, (10) 11, 535;
Charles C. price, J. Am. Chem. Soc, 1943, 65, 439;
E. S. Pokrovskaya, J. Gen. Chem. (USSR), 1939, 9, 1953.

This method leads to a low yield and an absence of selectivity and, furthermore, it is not economical.

Patents or patent applications DE-C-638 756, DE-A 2 208 363, U.S. Pat. No. 2,229,018, and U.S. Pat. No. 3,736,106 describe the alkylation of aromatic compounds by olefins, for instance cyclic olefins, in the presence of catalysts which are clays, for instance montmorillonite, kaolin, hydrosilicates and bleaching earths. These methods are not selective.

U.S. Pat. Nos. 2,904,607, 3,641,177, 4,393,262, DE-A-3 334 084, EP-A-280 055, J. Catal. 1986, 101, page 273 describe the alkylation of aromatic products using zeolites as catalysts, with linear alkylation agents such as, for example, olefins having 2 to 4 carbon atoms or methanol. These documents do not describe the alkylation of aromatic products with cyclic alkyl groups.

Patent Application DE-A-1 934 426 describes a continuous method of preparing alkylated aromatic compounds. That application cites numerous catalysts of zeolite type, for instance natural zeolites, such as gmelinite, dachiardite, faujasite, heulandite and mordenite or synthetic zeolites, such as omega L and Y zeolites. That application also mentions numerous aromatic compounds and a large variety of alkylation agents. This method is carried out in two steps. In a first step, the alkylation is effected with an alkylation agent in the presence of zeolites suspended in the liquid medium. The alkylation is not selective, and a mixture of mono- and polyalkylaromatics is obtained. In order to remedy this absence of selectivity, in a second step the reaction medium obtained from the first step is contacted with a zeolite, without a suspension and without an alkylating agent, so as to effect a transalkylation. Despite this second step, the overall selectivity at the end of these two steps remains low.

U.S. Pat. No. 4,230,894 describes the nonselective alkylation of benzene or alkylbenzene in order to obtain a mixture of isomers which is contacted with a zeolite so as to crack or selectively transalkylate the 1,4-dialkylbenzene isomer in order to enrich the mixture with 1,3-dialkylbenzene isomer.

Patent Application PCT/CH 90/00178 incorporated here by reference describes a method of cycloalkylating naphthalene with at least one cyclic group, this method being characterized by the following points:

(a) as catalyst, there is used at least one zeolite of faujasite structure having pore openings of more than 6.7 Å, the silica/alumina weight ratio of this zeolite being greater than 2.5, and its residual concentration in alkaline ion(s) being less than 3% in weight.

(b) the reaction is carried out batch-wise in heterogenous liquid/solid phase at a temperature of between 20° C. and 250° C. under a pressure of at most 30 bars, the zeolite or zeolites being suspended in the reaction medium;

(c) the alkylating-agent/naphthalene molar ratio is at least equal to 1.

SUMMARY OF THE INVENTION

The object of the present invention is to provide a method of preparing an alkylated aromatic product by alkylation of at least one aromatic compound using at least one zeolite as catalyst, this alkylation giving several alkylated aromatic products. This method is characterized by high yields of the desired alkylated aromatic product as a result of the transformation of the by-products of the reaction.

The method of the invention is characterized by the following points:

(a) the initial aromatic compound is reacted with at least one alkylating agent in the presence of at least one zeolite as catalyst, referred to as "alkylation zeolite";

(b) the desired alkylated aromatic product is then separated by crystallization from the products of the alkylation;

(c) the uncrystallized part of the alkylated aromatic products is subjected to a dealkylation in the presence of at least one zeolite as catalyst, referred to as "dealkylation zeolite" so as to regenerate the initial aromatic compound;

(d) the regenerated aromatic compound is recycled in order to react it again with the alkylating agent, in the presence of the alkylation zeolite.

The method of the invention is particularly suitable for the cycloalkylation of naphthalene in order to obtain 2,6-dicycloalkyl naphthalenes.

The alkylation reagents must contain at least one double bond, or a reactive group, for instance a halogen or an OH group, such reagents being, for instance, cyclohexene, chloro- or bromo-cyclohexane and cyclohexanol.

The zeolites used in the method of the invention may be in proton form or be exchanged by cations, in particular rare earth cations (for instance, La, Ce, Pr, Gd, Yb).

The invention also concerns the alkylated aromatic compounds obtained by the method described above, in particular 2,6-dicyclohexyl naphthalene. This product is very important in polymer chemistry since it makes it possible by oxidation to obtain compounds containing hydroxyl or carboxyl groups in 2,6 position, these products serving in particular for the synthesis of aromatic polyamides or polyesters.

DESCRIPTION OF THE DRAWINGS

The invention will easily be understood on the basis of the following examples and the figures relating to these examples.

FIG. 1 shows the general scheme of a method in accordance with the invention. This method consists essentially in effecting the cyclohexylation of the naphthalene by reaction of bromocyclohexane with naphthalene in the presence of a zeolite as catalyst in order to obtain 2,6-dicyclohexyl naphthalene and then effecting the subsequent dealkylation of the alkylated by-products of the naphthalene in the presence of a zeolite as catalyst in order to regenerate the naphthalene, Which is then recycled into the alkylation step.

FIG. 2 shows the scheme of a possible purification of 2,6-dicyclohexyl naphthalene, and FIG. 3 shows the scheme of a possible purification carried out on the naphthalene after dealkylation before recycling for alkylation. These FIGS. 2 and 3 concern modifications which may be made in the method according to FIG. 1, and these modifications will be described subsequently.

Figure 1:
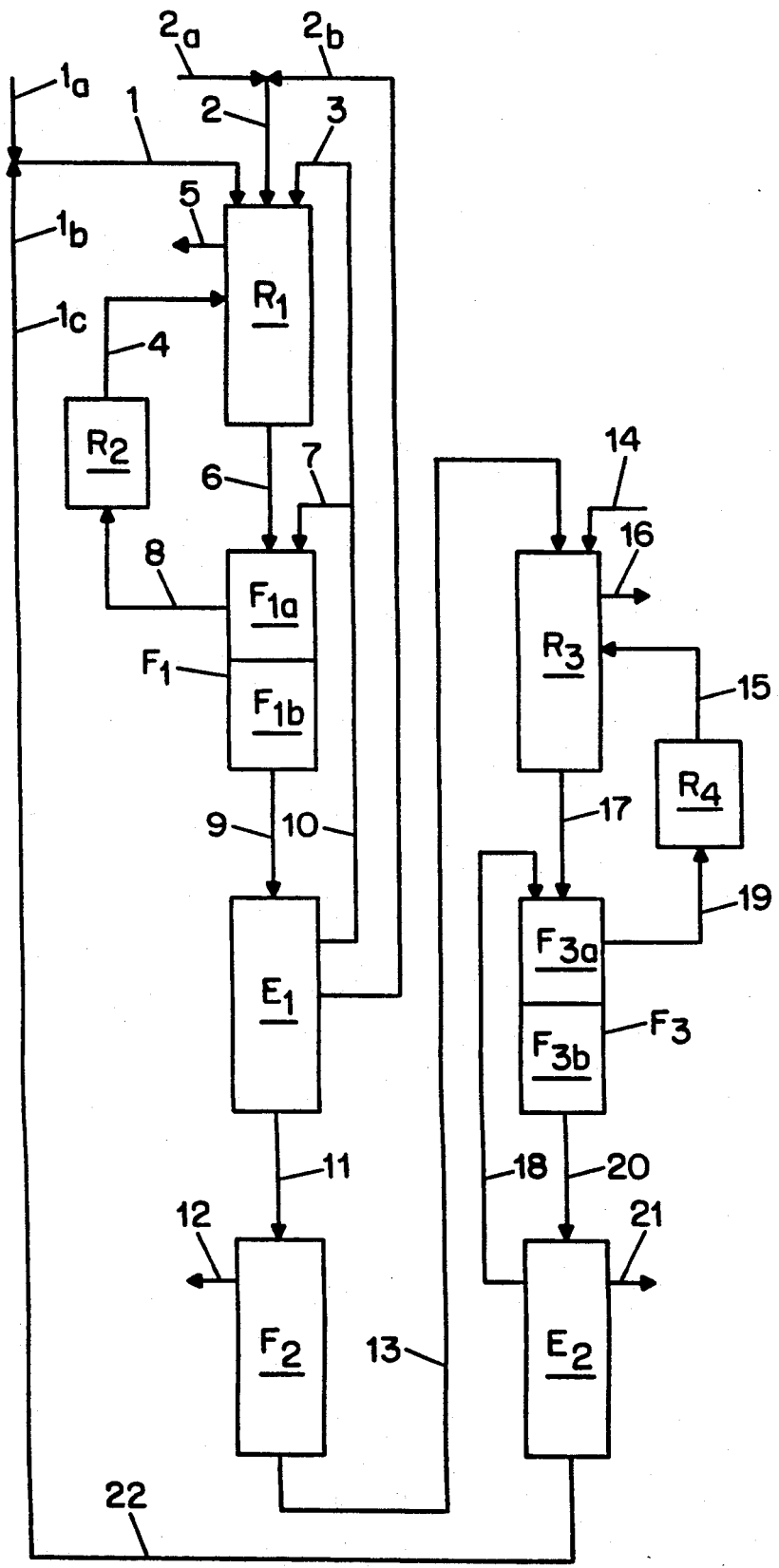
FIG. 1 shows the scheme of a method in accordance with the invention.
Figure 2:
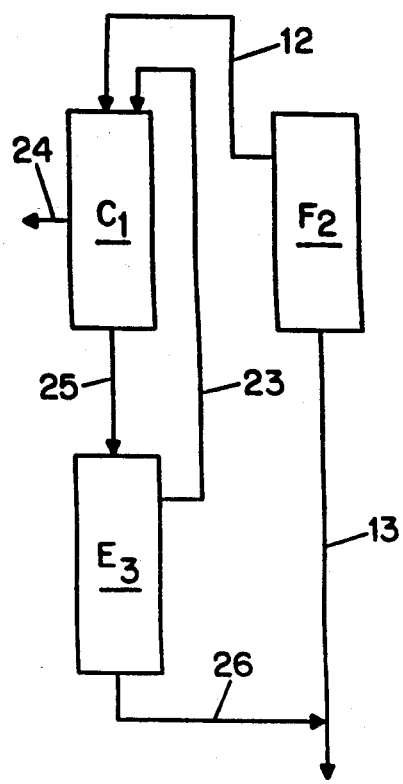
FIGS. 2 and 3 each show a partial diagram corresponding to a modification of the scheme shown in FIG. 1 in accordance with other variants of the method in accordance with the invention.
Figure 3:
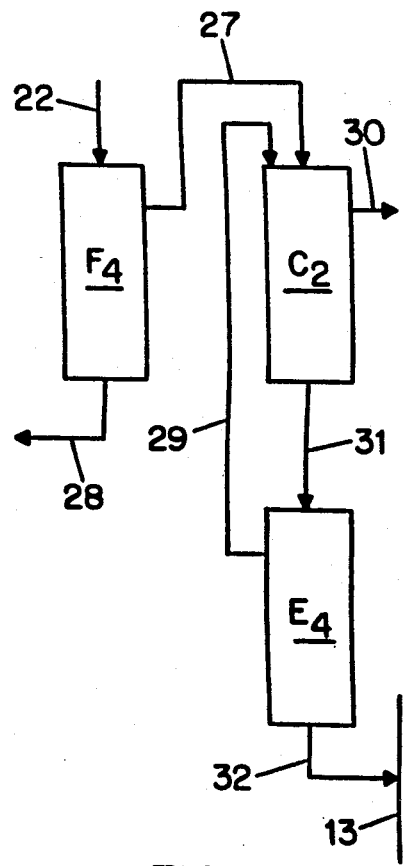

For purposes of simplification, the products used or obtained in the methods described are represented in FIGS. 1 to 3 by lines which have arrows to indicate the direction of flow of these products.

DESCRIPTION OF THE INVENTION

In the following description, the same zeolite is used for the alkylation reaction as for the dealkylation reaction. This zeolite, known as ZF-520, is marketed by the Zeocat Company.

The properties of this zeolite of faujasite structure, which is used in the form of a powder, are given in the following Table 1.

TABLE 1

| % By Weight | | | Molar Ratio | Specific Surface | Pore |
|---|---|---|---|---|---|
| $S_iO_2$ | $Al_2O_3$ | $Na_2O$ | $S_iO_2/Al_2O_3$ | $(m^2/g)$ | Size Å |
| 95.8 | 4.1 | 0.14 | 40 | 800 | 8 |

Before use, this zeolite is activated by heating it in an oven in the following manner:

The increase in temperature in the oven is from 20° C. to 300° C. at the rate of 50° C./hour. The temperature is maintained at 300° C. for 6 hours, whereupon cooling is effected to 200° C. at the rate of 40° C./hour, this calcining heat treatment being carried out in a stream of air of 200 cm$^3$/minute.

The analyses of the products are carried out with a DELSI gas chromatograph Series 330 equipped with an OVI capillary column of 25 m, followed by a flame ionization detector. It is coupled to a DELSI ENICA 21 integrator. Nitrobenzene is used as internal standard and it is added in the samples serving for the analysis.

The chromatographic analysis conditions are as follows:
temperature of the injector: 330° C.;
temperature of the detector: 320° C.;
programming of the temperature of the oven: heating from 100° C. to 280° C., the rate of heating being 15° C./min;
pressure of the hydrogen serving as carrier gas: 0.65 bar.

The determination of the structure of the products of the reaction is effected by an arrangement formed by a gas chromatograph coupled with a mass spectrometer. The chromatograph is equipped with a capillary column of type OVI of 25 m.

The analysis conditions with this unit are as follows:
temperature of the injector: 250° C.;
temperature of the detector: 250° C.;
programming of the temperature of the oven: heating from 100° C. to 280° C. with an increase in temperature of 10° C./min;
pressure of the helium used as carrier gas: 0.5 bar.

In order to simplify the description, the abbreviations used in this specification are as follows:
Naphthalene: NP; Bromocyclohexane: BCH;
Cyclohexane: CHA; 2,6-dicyclohexylnaphthalene; 2,6 DCN; monocyclohexyl-naphthalenes: MCN;
dicyclohexylnaphthalenes: DCN; Cyclohexene: CHE; Zeolite: ZE.

1. Alkylation of the naphthalene and separation of the 2,6-dicyclohexylnaphthalene The method used for this alkylation is in accord with the aforementioned Patent Application PCT/CH 90/00178.

The alkylation is carried out in the static reactor $R_1$, which is an autoclave of 100 ml (100 cm$^3$) manufactured by the BURTON-CORBLIN Company, comprising an internal rotary agitator with magnetic drive, a pressure gauge, and an apparatus for measuring the speed of rotation.

The autoclave $R_1$ is heated by an oven the temperature regulation of which is assured by a regulator manufactured by the SOTELEM Company.

Naphthalene (NP), bromocyclohexane (BCH), cyclohexane (CHA), zeolite ZF-520 (ZE) and a recovery mixture containing various naphthalene compounds other than NP are introduced into the reactor $R_1$, this being done in the following manner:
NP introduced 1: 6.4 g (50 mmols), namely;
make-up NP $1_a$: 3.3 g (25.8 mmols);
recovery NP $1_b$: 3.1 g (24.2 mmols);
BCH introduced 2: 16.2 g (100 mmols), namely;
make-up BCH $2_a$: 14.0 g (86.4 mmols);
recovery BCH $2_b$: 2.2 g (13.6 mmols);
CHA introduced 3: 50 cm$^3$ coming entirely from the recovery;
ZE introduced 4: 1.0 g coming entirely from the recovery;
Recovery mixture $1_c$ (3.5 g) containing various naphthalene compounds other than NP. This mixture constitutes with $1_b$ a crude recovered dealkylation product.

This introduction is carried out under ambient conditions, the temperature and the pressure in the reactor being then about 20° C. and 1 bar respectively.

The above-mentioned recoveries, as well as the recoveries which follow, correspond to a prior preparation in accordance with the invention, since the method described is a batch method.

The reaction mixture is then agitated in the reactor $R_1$ with a speed of 680 rpm, after closing the reactor. There is thus obtained a suspension of the catalyst in the reaction medium. The temperature of the reactor is increased from about 20° C. to 200° C. in 10 minutes and the agitation and heating are stopped as soon as the temperature of the reactor reaches 200° C., the autogenous pressure in the reactor being then 15 bars. The maximum temperature and pressure conditions in the reactor upon the alkylation being therefore 200° C. and 15 bars respectively.

The alkylation reaction carried out in heterogenous liquid/solid phase in the reactor $R_1$ is as follows:

CHA is a solvent of NP, BCH and alkylated aromatic products.

The reactor $R_1$ is then allowed to cool. When its temperature reaches 20° C., it is opened and gaseous HBr 5 produced by the alkylation escapes to the outside of the reactor $R_1$.

The reaction mixture 6 is then introduced into the filter $F_1$. This two-stage filter $F_1$ consists of two individual filters.

The first filter $F_{1a}$ in the upper part of $F_1$ consists of fritted glass, while the second filter $F_{1b}$ in the lower part consists of fritted glass as support for activated charcoal.

The filter $F_{1a}$ makes it possible to separate the ZE, which is washed with 50 cm$^3$ of recovery CHA 7, After washing, the ZE 8 is introduced into the oven $R_2$. The oven $R_2$ makes it possible to regenerate the ZE by subjecting it to the activation treatment previously described. The ZE 4 thus regenerated is then introduced into the reactor $R_1$ as previously described.

The filter $F_{1b}$ makes it possible to obtain a clear filtrate 9 (100 ml), which is introduced into the evaporator $E_1$. The evaporator $E_1$ makes it possible to recover two light fractions. One 10 is formed of CHA (100 ml) and the other 2b of BCH (2.2 g, namely 13.6 mmols). The CHA 10 gives the two feeds 7 and 3 previously described. The BCH 2b feeds the reactor $R_1$ as previously described. The crude product 11 (12.09 g) obtained after treatment in the evaporator $E_1$ emerges from $E_1$. This crude product, at room temperature, is in the form of two clearly distinct phases a solid phase formed of crystals of 2,6 DCN and a liquid phase corresponding to the mixture of NF, MCN, DCNs other than 2,6 DCN and various other naphthalene products.

The product 11 arrives in the filter $F_2$ which makes it possible to separate the solid product 12 (2.1 g) containing 96% by weight of 2,6 DCN (6.9 mmols) and 4% by weight of MCN (0.4 mmols).

The filtrate 13 (9.9 g) coming from the filter $F_2$ is a mixture of naphthalene compounds, this mixture being impoverished in 2,6 DCN (0.7 g, namely 2.4 mmols). The filtrate 13 is then subjected to the naphthalene regeneration treatment described below.

2 - Regeneration of naphthalene

This regeneration phase employs the reactor $R_3$. The construction of this reactor $R_3$ as well as the means for heating it are similar to those previously described for the reactor $R_1$.

The following products are introduced into the reactor $R_3$:
the filtrate 13 (9.9 g), which is a mixture of NP, MCN and DCN
CHA 14 (50 cm$^3$);
ZE 15 (1.0 g) which is recovered ZE.

This introduction is effected under ambient conditions, the temperature and the pressure in the reactor being about 20° C. and 1 bar respectively.

The reactor is agitated at 680 rpm after having closed it, and it is heated in such a manner that its temperature rises from about 20° C. to 300° C. in 18 minutes. In this way, a suspension of the catalyst in the reaction medium is obtained.

As soon as the temperature reaches 300° C., the agitation and the heating are both stopped, the autogenous pressure in the reactor $R_3$ being 50 bars at 300° C. The maximum conditions of temperature and pressure in the reactor upon the dealkylation are therefore 300° C. and 50 bars respectively.

In this reactor, upon heating, the following reaction takes place in liquid/solid heterogenous phase:

$$MCN + DCN \rightarrow NP + CHE + H_2$$

the dealkylation therefore giving naphthalene, cyclohexene and hydrogen.

When the temperature of the reactor $R_3$ reaches 20° C. at the end of the cooling, the reactor is opened and hydrogen 16 is released.

The heterogenous mixture 17 emerging from the reactor $R_3$ is introduced into the two-step filter $F_3$ comprising the individual filters $F_{3a}$ and $F_{3b}$, the arrangement of the filter $F_3$ being identical to that of the filter $F_1$.

The upper filter $F_{3a}$ makes it possible to separate ZE, which is washed with a recovered mixture 18 (50 cc) of CHA and CHE.

The ZE 19 emerging from the filter $F_3$ is introduced into the oven R4 where it undergoes the same regeneration treatment as that effected in the oven $R_2$, after alkylation. The activated zeolite 15 emerging from the oven R4 is introduced into the reactor $R_3$, as previously described.

The liquid 20 (100 cc) emerging from the lower stage $F_{3b}$ of the filter $F_3$ is a clear liquid formed of the filtrate of the mixture 17 and of the wash liquid 18. This liquid 20 is introduced into the evaporator $E_2$. The evaporation gives a mixture of CHA and CHE (100 cc), a part 18 of which serves for the washing in the filter $F_3$, as previously described, while the other part 21 (50 cc) is stored for other uses.

The dealkylation product 22 emerging as residue from the evaporator $E_2$ (6.6 g) is a mixture enriched in NP (3.1 g, namely 24.2 mmols). This product is present at room temperature in the form of two separate phases—a solid phase formed of NP crystals and a liquid phase corresponding to a mixture of various naphthalene compounds.

This product 22 is recycled into the alkylation reactor $R_1$, the solid phase of 22 thus corresponding to the feed 1b (NP) and the liquid phase of 22 thus corresponding to the feed $1_c$ with have been previously described in the alkylation step.

The yield of 2,6 DCN of the method of the invention corresponds to the molar ratio

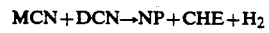

$$\frac{\text{2,6 DCN produced (contained in 12)}}{\text{make-up NP } 1_a}$$

This ratio is 26.7%.

The method of the invention is simple to carry out and gives a high yield of 2,6-dicyclohexyl naphthalene.

By way of comparison, the known methods using aluminum chloride as catalyst have the following drawbacks:
- the aluminum chloride forms complexes with the naphthalene derivatives and tends to contaminate the products, which leads to the necessity of carrying out several successive washings.
- The aluminum chloride cannot be used again and raises the problem of the use of the undesirable by-products.
- The aluminum chloride does not permit working with an excess of bromocyclohexane; thus, at the end of the reaction, one has a large amount of naphthalene which it is necessary to recover by distillation before treating the mixture of mono- and poly- alkylnaphthalenes, so that the yield of 2,6 dicyclohexyl naphthalene is very low, less than 5%.

The product 12 obtained after filtration in $F_2$ is sufficiently rich in 2,6 DCN to be used as such, for instance, for a subsequent chemical synthesis. One can also recrystallize the 2,6 DCN contained in the product 12, as shown for instance in the diagram of FIG. 2. The product 12 is then introduced into the crystallizer $C_1$, which receives a feed 23 (100 ml) of recovered boiling ethanol. One thus obtains 100% pure 2,6 DCN, 24, (2.0 g, namely 6.7 mmols). The filtrate 25 coming from the crystallizer $C_1$ is introduced into the evaporator $E_3$ which makes it possible to recover the ethanol 23, which is recycled into the crystallizer $C_1$. The residue 26 (0.1 g) coming from the evaporator $E_3$ is a mixture of MCN and 2,6 DCN. This product 26 can be added to the filtrate 13 coming from the filter $F_2$ and introduced into the dealkylation reactor $R_3$.

The crude product 22 coming from the evaporator $E_2$ can be recycled directly into the alkylation reactor $R_1$ as previously described. However, the product 22 can also be enriched in NP, as shown in the diagram of FIG. 3.

The product 22 is introduced into the single filter $F_4$. In this way 22 is separated into a solid phase 27 (0.9 g) which is strongly enriched in Np (89%, namely 6.3 mmols of NP), and a liquid phase 28 (5.7 g) formed of a mixture of NP and of various alkyl naphthalenes, this phase containing 40% NP. This phase 28 is recycled into the dealkylation reactor $R_3$. The solid phase 27 is introduced into the crystallizer $C_2$ where the NP is crystallized by introduction of recovered ethanol 29 (25 ml). The recrystallized NP 30 is recycled into the alkylation reactor $R_1$. The liquid 31 coming from the crystallizer $C_2$ is introduced into the evaporator $E_4$, which makes it possible to separate 31 into ethanol 29, which is recycled into the crystallizer $C_2$, and into a residue 32, formed of various alkyl naphthalenes. The residue 32 is recycled with 13 into the dealkylation reactor $R_3$.

Preferably, the following characteristics are present in the alkylation reactor $R_1$ for the preparation of 2,6 DCN:

the maximum temperature is at least equal to 140° C. and at most equal to 220° C.;
the maximum pressure is at least equal to 5 bars and at most equal to 30 bars;
the molar ratio alkylation agent/naphthalene is at least equal to 1.5 and at most equal to 4 at the start of the alkylation.

Preferably, in the dealkylation reactor $R_3$, the maximum temperature at least equal to 260° C. and at most equal to 350° C., and the maximum pressure is at least equal to 10 bars and at most equal to 60 bars, for the preparation of the 2,6 DCN.

Of course, the invention is not limited to the examples which have been described above. Thus, for instance, the invention applies to the alkylation of compounds other than naphthalene and/or to the use of alkylation agents other than bromocyclohexane in the event that the desired alkylated product crystallizes from the products of the alkylation reaction. Zeolites other than ZF-520 can be used for the alkylation and/or dialkylation. These other zeolites, having preferably the same definition as for the zeolites of previously mentioned application PCT/CH90/00178, can be for instance zeolites ZF-510 and ZF-515 from the Zeocat Company, the molar ratio $SiO_2/Al_2O_3$ being equal to 20 for ZF-510 and equal to 30 for ZF-515.

The invention also applies to cases in which several aromatic compounds are alkylated in the same operation with several alkylating agents and to cases in which several zeolites are used for the alkylation operation and/or for the dealkylation operation. Furthermore, the alkylation zeolites can be the same as or different from the dealkylation zeolites.

The invention also applies to the case that the alkylation and/or dealkylation is carried out continuously.

We claim:

1. A method for preparing a selected alkylaromatic compound comprising the steps of:
    (a) reacting an aromatic compound with an alkylating agent in the presence of a first zeolite under conditions such that the first zeolite catalyzes the reaction of the aromatic compound with the alkylating agent to form a plurality of alkylated aromatic products including the selected alkylaromatic compound;
    (b) selectively crystallizing the selected alkylaromatic compound;
    (c) separating the crystallized alkylaromatic compound from the other uncrystallized alkylated aromatic products;
    (d) dealkylating the uncrystallized alkylated aromatic products in the presence of a second zeolite, different from the first zeolite, under conditions such that the second zeolite catalyzes the regeneration of the aromatic compound; and
    (e) recycling the regenerated aromatic compound as a feedstock for the reaction of step (a).

2. A method according to claim 1, wherein the selected alkylaromatic compound is a cycloalkylaromatic compound and the alkylating agent is selected from the group consisting of cycloalkenes and derivatives of cycloalkanes containing a reactive group.

3. A method according to claim 2, wherein the selected cycloalkylaromatic compound is 2,6-dicyclohexylnaphthalene, the aromatic compound is naphthalene, and the alkylating agent is selected from the group consisting of cyclohexene and derivatives of cyclohexane containing a reactive group.

4. A method according to claim 3, wherein the temperature during alkylation is at least equal to 140° C. and at most equal to 220° C., and the pressure is at least equal to 5 bars and at most equal to 30 bars.

5. A method according to claim 3, wherein at the start of the alkylation, the alkylation agent/naphthalene molar ratio is at least equal to 1.5 and at most equal to 4.

6. A method according to claim 3, wherein upon the dealkylation, the maximum temperature is at least equal to 260° C. and at most equal to 350° C. and the maximum pressure is at least equal to 10 bars and at most equal to 60 bars.

7. A method according to claim 1, wherein the alkylation zeolite and/or the dealkylation zeolite are suspended in a reaction medium.

8. A method according to claim 1, wherein the method is discontinuous.

9. A method according to claim 1, wherein the first zeolite and/or the second zeolite are zeolites of faujasite structure having pore openings of more than 6.7 Å, the silica/alumina weight ratio of these zeolites being greater then 2.5, and their residual concentration of alkaline ion(s) being less than 3% by weight.

10. A method for preparing a selected alkylaromatic compound comprising the steps of:
  (a) reacting an aromatic compound with an alkylating agent in the presence of a zeolite under a first set of conditions such that the zeolite catalyzes the reaction of the aromatic compound with the alkylating agent to form a plurality of alkylated aromatic products including the selected alkylaromatic compound;
  (b) selectively crystallizing the selected alkylaromatic compound;
  (c) separating the crystallized alkylaromatic compound from the other uncrystallized alkylated aromatic products;
  (d) dealkylating the uncrystallized alkylated aromatic products in the presence of the zeolite under a second set of conditions, different from the first set of conditions, such that the zeolite catalyzes the regeneration of the aromatic compound; and
  (e) recycling the regenerated aromatic compound as a feedstock for the reaction of step (a).

11. A method according to claim 10, wherein the selected alkylaromatic compound is a cycloalkylaromatic compound and the alkylating agent is selected from the group consisting of cycloalkenes and derivatives of cycloalkanes containing a reactive group.

12. A method according to claim 11, wherein the selected cycloalkylaromatic compound is 2,6-dicyclohexylnaphthalene, the aromatic compound is naphthalene, and the alkylating agent is selected from the group consisting of cyclohexene and derivatives of cyclohexane containing a reactive group.

13. A method according to claim 12, wherein the temperature during alkylation is at least equal to 140° C. and at most equal to 220° C., and the pressure is at least equal to 5 bars and at most equal to 30 bars.

14. A method according to claim 13, wherein at the start of the alkylation, the alkylation agent/naphthalene molar ratio is at least equal to 1.5 and at most equal to 4.

15. A method according to claim 13, wherein the temperature during the dealkylation is at least equal to 260° C. and at most equal to 350° C. and the pressure is at least equal to 10 bars and at most equal to 60 bars.

16. A method according to claim 10, wherein the method is discontinuous.

17. A method according to claim 10, wherein the zeolite has a faujasite structure having pore openings of more than 6.7 Å, the silica/alumina weight ratio of the zeolites being greater than 2.5, and its residual concentration of alkaline ion(s) being less than 3% by weight.

18. A method according to claim 10, wherein the first and second sets of conditions are different in temperature.

* * * * *

UNITED STATES PATENT AND TRADEMARK OFFICE
CERTIFICATE OF CORRECTION

PATENT NO. : 5,210,350
DATED : May 11, 1993
INVENTOR(S) : Solofo et al.

It is certified that error appears in the above-identified patent and that said Letters Patent is hereby corrected as shown below:

Col. 3, line 7, "Which" should read --which--;

Col. 5, line 34, "NF" should read --NP--;

Col. 6, line 46, "with have" should read --which have--;

Col. 7, line 54, "temperature" should read --temperature is--;

Col. 7, bridging lines 65-66, "dialkylation" should read --dealkylation--;

Col. 10, line 11, "claim 14" should read --claim 12--;

Col. 10, line 14, "claim 15" should read --claim 12--.

Signed and Sealed this

Fifteenth Day of March, 1994

Attest:

BRUCE LEHMAN

*Attesting Officer*    *Commissioner of Patents and Trademarks*